(12) United States Patent
Tan et al.

(10) Patent No.: US 6,367,310 B1
(45) Date of Patent: Apr. 9, 2002

(54) DRAINAGE TESTING OF POROUS ASPHALT ROAD MIXES

(75) Inventors: Siew Ann Tan; Tien Fang Fwa; Chip Tiong Chuai, all of Singapore (SG)

(73) Assignee: National University of Singapore, Crescent (SG)

( * ) Notice: Subject to any disclaimer, the term of this patent is extended or adjusted under 35 U.S.C. 154(b) by 0 days.

(21) Appl. No.: 09/673,318
(22) PCT Filed: Mar. 30, 1999
(86) PCT No.: PCT/SG99/00022
  § 371 Date: Feb. 20, 2001
  § 102(e) Date: Feb. 20, 2001
(87) PCT Pub. No.: WO99/53294
  PCT Pub. Date: Oct. 21, 1999

(30) Foreign Application Priority Data

Apr. 15, 1998 (SG) .............................. 9800747

(51) Int. Cl.⁷ .............................................. G01N 15/08
(52) U.S. Cl. ............................................................. 73/38
(58) Field of Search .............................................. 73/38

(56) References Cited

U.S. PATENT DOCUMENTS

| | | | |
|---|---|---|---|
| 2,949,766 A | 8/1960 | Kirkham et al. | |
| 3,548,635 A | 12/1970 | Hutchinson et al. | |
| 3,861,196 A * | 1/1975 | Domenighetti ............... | 73/38 |
| 4,070,903 A | 1/1978 | Lees et al. ................... | 73/38 |
| 4,164,139 A | 8/1979 | Jones ........................... | 73/38 |
| 5,157,959 A * | 10/1992 | Ankeny et al. .............. | 73/38 |
| 5,780,720 A * | 7/1998 | Swain ........................... | 73/38 |

FOREIGN PATENT DOCUMENTS

| | | | |
|---|---|---|---|
| DE | 129934 | 2/1978 | ................ 73/38 |
| DE | 246169 | 5/1987 | |

OTHER PUBLICATIONS

G. Van Heystraeten et al., "Ten Years' Experience of Porous Asphalt in Belgium", Transportation Research Record 1265, pp. 34–41, 1990.

Lyle K. Moulton et al., "Determination of the In Situ Permeability of Bases and Subbases", Public Roads, pp. 134–141, Mar. 1980.

Thomas Isenring et al., "Experiences with Porous Asphalt in Switzerland", pp. 41–53, 1990.

Aurelio Ruiz et al., Porous Asphalt Mixtures in Spain, Transportation Research Record 1265, pp. 87–94, 1990.

* cited by examiner

Primary Examiner—Daniel S. Larkin
(74) Attorney, Agent, or Firm—Birch, Stewart, Kolasch & Birch, LLP

(57) ABSTRACT

A field permeameter for performing a falling head permeability test on porous road surfaces with three-dimensional flow through the road surface or test slab comprises a clear plastic cylinder (1), and a rubber lined base flange (5, 6) to seal the test cylinder against the road surface during operation. A trap or valve assembly (7, 8, 9) in the closed position permitting the setting up of the falling head test at any desired initial head water level in the test cylinder. The activation of the test being initiated by the sudden release of the trap (8) which causes the water retained in the cylinder to flow through the test road section. The falling head of water through the road being measured by a submersible pressure transducer (3) at the base of the cylinder. From the falling head data, and the conversion factors for converting three-dimensional to one-dimensional flow property, the permeability (k) and the flow exponent (m) of the porous road specimen can be determined.

12 Claims, 2 Drawing Sheets

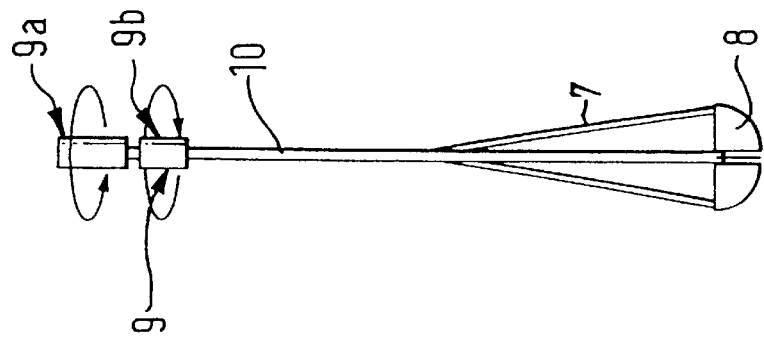
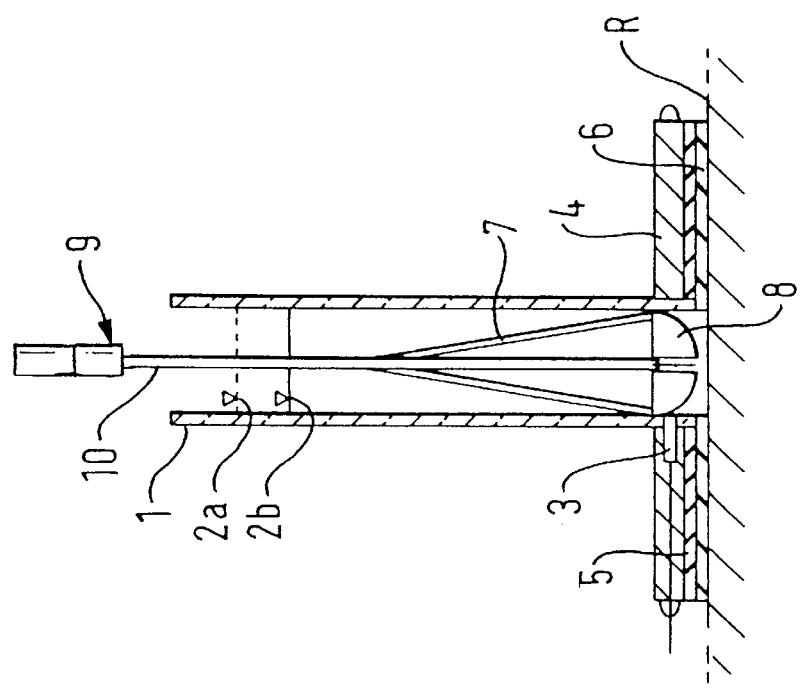
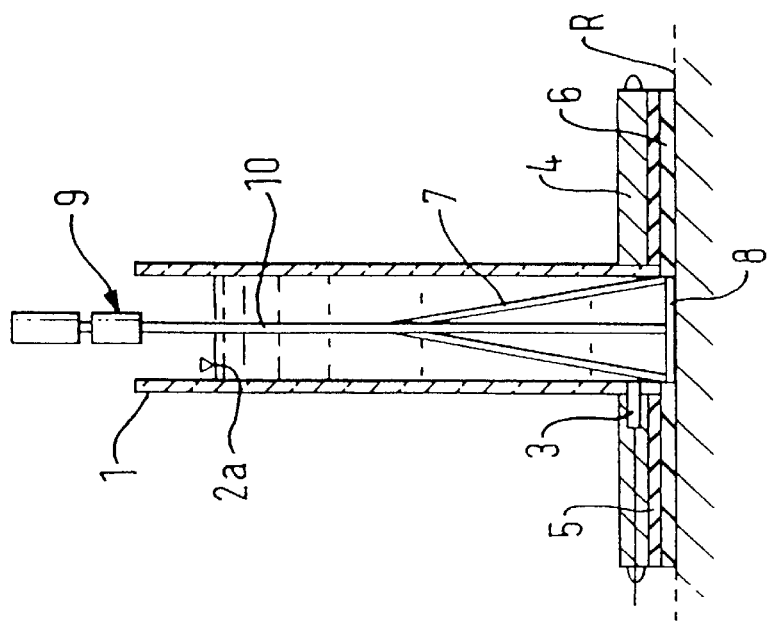

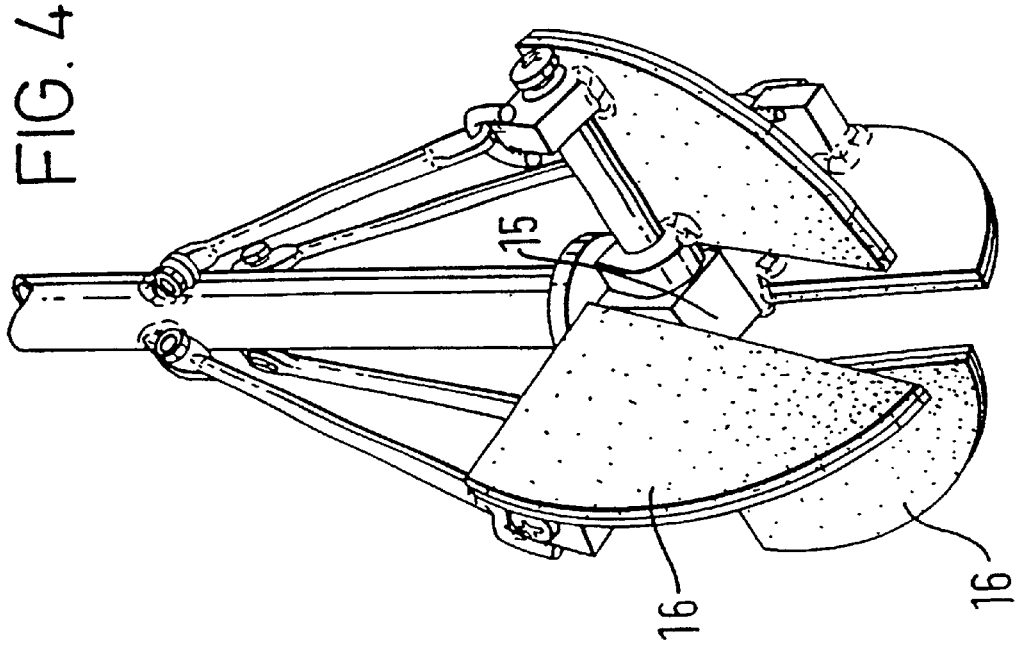
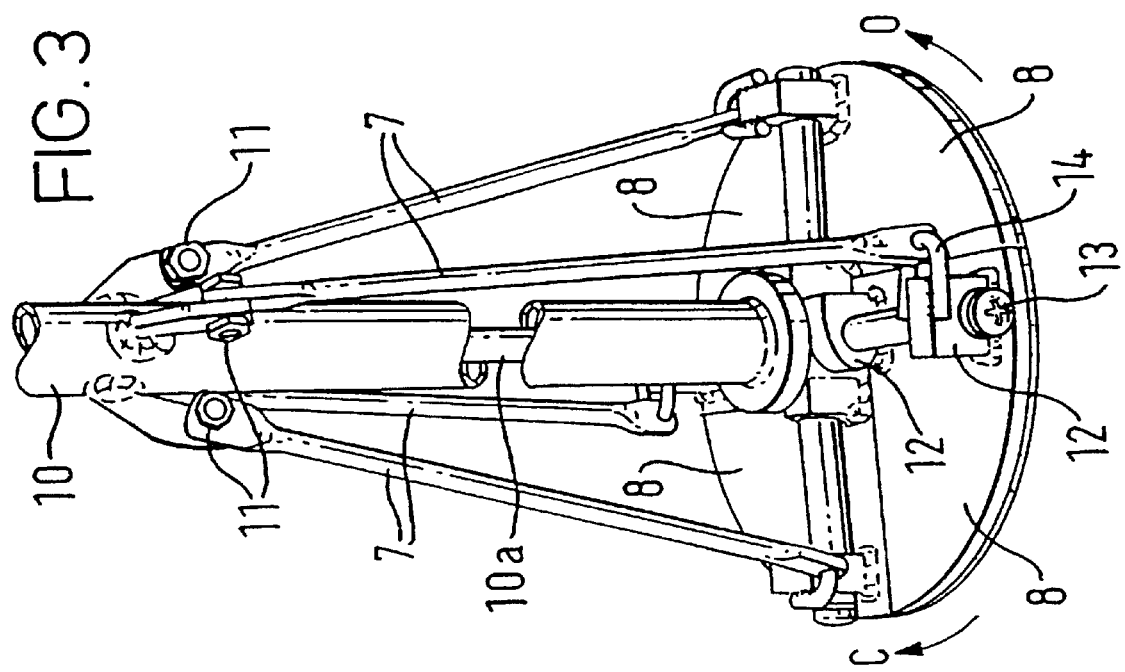

DRAINAGE TESTING OF POROUS ASPHALT ROAD MIXES

This application is the national phase under 35 U.S.C. § 371 of PCT International Application No. PCT/SG99/00022 which has an International filing date of Mar. 30, 1999, which designated the United States of America.

FIELD OF INVENTION

This invention relates to a portable apparatus primarily for use in the field and for measuring the drainage performance of porous asphalt road mixes, using the falling head principle. Porous road mixes are relatively new road making materials in the road industry particularly in South East Asia.

BACKGROUND OF THE INVENTION

With porous (or drainage) road mixes there is no systematic way of measuring the drainage performance. The impetus for use of these types of mixes in the tropics with high and frequent rainfall is their ability to rapidly drain off rain water so as to provide a dry riding surface even in heavy downpours. This will greatly enhance road safety as a dry riding surface would eliminate the problem of wet skidding, aquaplaning, and reduced visibility caused by surface water spray from vehicle tires.

There are some existing field apparatus for comparing the drainage capability of porous asphalt road slabs. These include a Belgian permeameter (Heystraeten, 1990), a Swiss IVT permeameter (Isenring et al, 1990), and a Spanish LCS drainometer (Ruiz et al, 1990). All these apparatus have the common feature of a transparent cylindrical tube in which the time for a falling head of water between a fixed distance along the tube is measured by a stop watch. Thus, by taking the measurement of time for a fixed volume of water to flow from the cylinder into the porous road slab, the average flow rate of the water discharge through the pavement can be estimated. This flow rate is then a kind of empirical measure of the drainage capability of the porous asphalt pavement. The variation in such equipment is basically: (a) size of cylindrical tube and volume of water used for test; (b) the way sealing is achieved between the cylinder and the road slab; (c) the way water is retained above the road slab before start of test; and (d) the way time is measured between the start to end of test. Presently, all existing apparatus do not have the sophistication to allow for a rational and objective determination of the permeability or drainage property of the porous road tested.

OBJECT OF THE INVENTION

One object of this invention is to provide a simple and inexpensive field apparatus which will enable the accurate measurement of the drainage property of porous road mixes using very simple technology and components. The device should be able to measure the permeability of porous road mixes using established fluid mechanics principles, where the permeability is a measure of the ease with which the mixes allow the flow of water through the pores.

In accordance with this invention, there is provided a field apparatus for the determination of the drainage properties of a porous asphalt road surface or slab in terms of its permeability coefficient (k) and flow exponent (m) using a falling head test method, which apparatus is characterised by:

(i) a water containing cylinder,
(ii) weighting means to provide pressure for sealing a rubber lined flanged base of the cylinder to the road surface,
(iii) a releasable means to provide a water retaining closure at the base of the cylinder to hold back water in the cylinder before the start of test, and to release the water suddenly from the cylinder onto the road surface at the start of test, and
(iv) a pressure transducer located in a lower part of the cylinder for measurement of the falling head of water in the cylinder during the test.

Features of this invention include the preferred use of a mechanical trap to retain water above the road slab before the start of test and to activate the sudden release of water at the start of test and the use of an accurate pressure transducer near the base of the tube to measure the falling head of water at small intervals, such as every millisecond. In addition, a theoretical basis is provided for reducing the falling head data to obtain a direct measure of the permeability of the porous road section tested.

DESCRIPTION OF DRAWINGS

This invention is further described and illustrated with reference to an embodiment shown by way of example in the drawings and wherein:

FIG. 1a shows one embodiment of this invention in side schematic sectional view with the trap closed, FIG. 1b shows the embodiment of FIG. 1a with the trap open, FIG. 2 shows schematically the trap door mechanism open, FIG. 3 shows a detail of the trap door mechanism closed, and FIG. 4 shows a detail as in FIG. 3, but with the trap door open.

Referring to FIGS. 1a and 1b of the drawings, these illustrate a schematic overview of the field permeameter showing a clear plastic vertical cylindrical tube 1, of dimension one metre in height by 150 mm internal diameter filled with water to the level 2a before the start of the test. An annular metal plate or plates 4 act as weights to provide pressure for sealing the rubber lined annular flange base 5 of the cylinder tube to the road surface R. An accurate pressure transducer 3 is located near the base of the cylinder for measuring the falling head of water during the test. A rubber base lining 6 provides a water tight seal between the cylindrical tube annular flange base 5 and the road surface R to be tested.

Referring to FIG. 2 the trap door device as shown has three components comprising the trap door handle 9, trap door rod/tube 10 and four rod linkages 7 all of stainless steel. A trap door base, which is of circular plan has four quadrant plates 8 which, in a closed position, provide a sealed base for retention of water in the cylindrical tube.

DESCRIPTION OF INVENTION

The permeability constant (k) for laminar flow through a saturated porous medium can be determined from Darcy's law, Equation 1:

$$v = \frac{Q}{A} = k\frac{\delta h}{t} = ki$$

where
v=specific discharge (m/s)
Q=fluid discharge at steady state (m$^{3/s}$)
A=Specimen cross section area (m$^2$)

k=permeability coefficient (m/s)

δh=hydraulic head difference held constant between inlet and outlet ends of specimen (m)

t=specimen thickness (m)

i=hydraulic gradient across specimen (m/m)

In general, the fluid flow through porous road mixes is neither laminar nor turbulent; the actual flow is a transition between the two regimes. Thus, the flow law governing drainage through porous road mixes is better described by Equation 2:

$$v=ki^m$$

where:

m is an experimentally determined exponent that describes the type of flow behaviour, m=1 for laminar flow, m=0.5 for turbulent flow, and m between 1 and 0.5 for transition from laminar to turbulent flows.

The proposed falling head apparatus can be used to determine both k and m experimentally to characterise fully the flow through a porous road mix.

The first preferred feature of this invention is the trap door mechanism shown in detail in FIGS. 2, 3 and 4. This mechanism consists of three components. The trap door handle 9 is made of two halves 9a and 9b. The upper half 9a of the handle is twisted in one direction relative to the lower half 9b, to close the trap door, and twisted again in the opposite direction to open the trap door. The trap door is supported by a thin rod with four linkages 7 of stainless steel. The base of the trap door is a circular four leaf quadrant 8, which when in closed position in FIG. 1a would form a circular plate of diameter slightly smaller than the internal diameter of the plastic tube 1 to provide a water tight seal in the base of the tube for filling up with water before the start of test. To start a test, the trap door handle can be twisted to open the trap door leaves 8 as in FIG. 1b, and water retained in the tube will suddenly be released (levels 2a to 2b) to flow through the porous road section being tested.

Referring to FIGS. 3 and 4, there is shown more specifically the arrangement of the trap valve assembly. The tube 10 embraces coaxially an inner rod 10a which extends from the bottom of tube 10 and carries a flange 15 with four laterally extending rods 13 forming pivots on which the leaves 8 forming the valve are mounted by lugs 12 allowing pivoting. The outer lugs 12 have links 14 which engage eyes in the end of rods 7 the other ends of which are bolted at 11 to the tube 10. When the inner rod 10a is rotated relatively to the tube 10, then flange 15 rotates also with rods 13 and through the linkage 14 causes the whole assembly carried by the flange 15 and rod 10a to move in the direction O and also downwardly, thus the leaves 8 pivot to the position shown in FIG. 4 to open the valve. Rotation in the opposite direction C pivots the leaves to the closed position.

In practice, the outer tube 10 is rotated by handle 9 whilst the inner rod 10a is held by handle 9a and the outer tube moves upwards a small amount there being provided a small gap between the handles for this purpose (see FIG. 1). The tips of the leaves 8 will in practice contact the road surface R during this action.

To assist the sealing action, the leaves 8 each have a rubber water seal segment 16.

The second preferred feature of this invention is the annular weight or weights 4 to provide the pressure to seal the rubber lined 6 base flange 5 of the cylindrical tube to the road surface, so that water from the cylinder will not leak between the base and the road surface during the falling head test.

The third essential feature of the invention is a sensitive pressure transducer 3 located near the base of the cylinder, which is used to measure accurately pressure changes of as little as 0.3 mm of water during the falling head test. This transducer 3 is activated at the start of test and with a simple data logger it can be set to measure the falling head in the cylinder 1 at one millisecond intervals.

The flow test in the field is a three-dimensional flow test, while the flow law of Equation 2 is a one-dimensional flow law. In order to fit the field falling head data to a one-dimensional flow law, research has produced a conversion factor to convert a field falling head determined k value to obtain the one-dimensional k value obtained from a laboratory test on a cylindrical specimen of the same material, satisfying Equation 2. With this conversion relationship, which is a function of the thickness and size of the test slab, the permeability of the porous specimen can be calculated by using the flow law of Equation 2 which accurately characterises the flow behaviour of porous mixes, being neither fully laminar nor fully turbulent in nature.

The prototype apparatus is fitted with a Druck pressure transducer with a 350 millibar pressure range. With a laptop PC, data logger falling head data at one millisecond interval with a precision of 0.03 mm can be captured. Using a spreadsheet program, the falling head data can be reduced to a velocity (v) versus head (h) relationship, from which the value of k and m for the three-dimensional flow case can be determined. Applying the correction factor for slab thickness and size effects, the equivalent k and m value for the one dimensional flow through a cylindrical specimen is obtained. This is an objective and rationally correct measure of the flow property of the porous slab tested by the portable field falling head apparatus.

An alternative to the trap door mechanism is to use a soft plastic bag in the shape of a cylindrical tube, with a loosely sealed end to retain a body of water in the cylinder before the start of the test. Both the mechanical trap door and the plastic bag alternative have been tested and it was found that the mechanical trap door provides more consistent and repeatable falling head test data than the latter.

This device can be applied in a number of situations with porous road mixes design and construction. It can be used to make objective comparisons of the drainage performance of alternative porous road mixes which are competing for the same job application. It can also be used to check on the drainage performance of newly laid roads as a means of quality control using a drainage performance criteria during road construction. It can also be applied for evaluating the deterioration of drainage performance of porous road mixes subject to clogging and blockage by fine silts and sands, weathering and traffic densification.

What is claimed is:

1. A field apparatus for the determination of the drainage properties of a porous asphalt road surface or slab using a falling head test method, said drainage properties including a permeability coefficient (k) and a flow exponent (m), said field apparatus comprising:

(i) a water containing cylinder having a rubber lined flanged base;

(ii) weighting means providing pressure for sealing the rubber lined flanged base of the cylinder to the road surface;

(iii) releasable means providing a water retaining closure at the base of the cylinder to hold back water in the cylinder before a start of testing, and to release the water suddenly from the cylinder onto the road surface at the start of testing; and (iv) a pressure transducer located in a lower part of the cylinder for measurement of the falling head of water in the cylinder during the test.

2. The apparatus in accordance with claim 1, said releasable means comprising:

a mechanical plate valve assembly at the base of the cylinder with a handle extending up through the cylinder, and a thin rod extending through the handle and coupled with the plate valve which can be opened or closed by actuating the handle.

3. The apparatus in accordance with claim 1, wherein said releasable means includes a trap mechanism allowing for a sudden release of water from the cylinder onto the porous road surface to start the falling head test instantaneously.

4. The apparatus in accordance with claim 1, further comprising:

said pressure transducer extending into the cylinder near the base thereof which can record falling head data to a precision of the order of 0.3 mm at intervals down to approximately one millisecond and operatively associated with a data logging and recording apparatus adapted to the pressure transducer used.

5. The apparatus in accordance with claim 2, wherein said releasable means includes a trap mechanism allowing for a sudden release of water from the cylinder onto the porous road surface to start the falling head test instantaneously.

6. The apparatus in accordance with claim 2, further comprising:

said pressure transducer extending into the cylinder near the base thereof which can record falling head data to a precision of the order of 0.3 mm at intervals down to approximately one millisecond and operatively associated with a data logging and recording apparatus adapted to the pressure transducer used.

7. The apparatus in accordance with claim 3, further comprising:

said pressure transducer extending into the cylinder near the base thereof which can record falling head data to a precision of the order of 0.3 mm at intervals down to approximately one millisecond and operatively associated with a data logging and recording apparatus adapted to the pressure transducer used.

8. A method for measuring the flow properties of a road surface, said method comprising:

interpreting falling head data from a three-dimensional flow test carried out on the road surface in order to obtain a permeability coefficient (k) and a flow exponent (m) of tested material that satisfy a one dimensional flow law in accordance with the function:

$$v=ki^m$$

where:

v=specific discharge (m/s)
k=permeability coefficient (m/s)
i=hydraulic gradient across specimen (m/m), and
m=experimentally determined exponent that describes the type of flow behavior,
m=1 for laminar flow,
m=0.5 for turbulent flow, and
m is between 1 and 0.5 for transition from laminar to turbulent flows;

releasing a column of water suddenly onto the road surface;

measuring and recording results of the fall in the head of water as a function of time; and processing the results to produce a number related to the permeability coefficient (k) and the flow exponent (m) for one-dimensional flow through a porous road specimen.

9. The method according to claim 8, wherein the column of water is released by a field apparatus for the determination of drainage properties of the tested material, said drainage properties including the permeability coefficient (k) and the flow exponent (m), said field apparatus comprising:

(i) a water containing cylinder having a rubber lined flanged base;

(ii) weighting means providing pressure for sealing the rubber lined flanged base of the cylinder to the tested material;

(iii) releasable means providing a water retaining closure at the base of the cylinder to hold back water in the cylinder before a start of testing, and to release the water suddenly from the cylinder onto the road surface at the start of testing; and (iv) a pressure transducer located in a lower part of the cylinder for measurement of the falling head of water in the cylinder during the test.

10. The method according to claim 9, wherein said releasable means includes a mechanical plate valve assembly at the base of the cylinder with a handle extending up through the cylinder, and a thin rod extending through the handle and coupled with the plate valve which can be opened or closed by actuating the handle.

11. The method according to claim 10, wherein said releasable means includes a trap mechanism allowing for a sudden release of water from the cylinder onto the porous road surface to start the falling head test instantaneously.

12. The method in accordance with claim 9, further comprising:

said pressure transducer extending into the cylinder near the base thereof which can record falling head data to a precision of the order of 0.3 mm at intervals down to approximately one millisecond and operatively associated with a data logging and recording apparatus adapted to the pressure transducer used.

* * * * *